US 7,397,894 B2

(12) United States Patent  (10) Patent No.: US 7,397,894 B2
Nakai et al.  (45) Date of Patent: Jul. 8, 2008

(54) TRANSMISSION IMAGER

(75) Inventors: Keisuke Nakai, Osaka (JP); Shigeru Sasakura, Osaka (JP); Masayuki Suzuki, Osaka (JP)

(73) Assignee: Pony Industry Co., Ltd., Osaka-shi, Osaka (JP)

( * ) Notice: Subject to any disclaimer, the term of this patent is extended or adjusted under 35 U.S.C. 154(b) by 0 days.

(21) Appl. No.: 10/565,745

(22) PCT Filed: Jul. 22, 2003

(86) PCT No.: PCT/JP03/09232

§ 371 (c)(1),
(2), (4) Date: Jan. 8, 2007

(87) PCT Pub. No.: WO2005/008227

PCT Pub. Date: Jan. 27, 2005

(65) Prior Publication Data

US 2007/0189450 A1    Aug. 16, 2007

(51) Int. Cl.
*H05G 1/65* (2006.01)
*G01B 1/02* (2006.01)
(52) U.S. Cl. ........................................ 378/98.8; 378/55
(58) Field of Classification Search ............ 378/51–57, 378/98.8, 68, 208
See application file for complete search history.

(56) References Cited

U.S. PATENT DOCUMENTS 3,989,944 A * 11/1976 Birks et al. .................... 378/71
6,630,676 B2 * 10/2003 Takemoto .............. 250/370.09
7,065,175 B2 * 6/2006 Green ............................ 378/57
2004/0120457 A1 * 6/2004 Karellas et al. ............... 378/62

FOREIGN PATENT DOCUMENTS

| JP | 2001-004559 | 1/2001 |
| JP | 2001-153819 | 6/2001 |
| JP | 2001203095 A | 7/2001 |
| JP | 2003-057195 | 2/2003 |
| KR | 1020070101203 A | 10/2007 |

* cited by examiner

*Primary Examiner*—Irakli Kiknadze
(74) *Attorney, Agent, or Firm*—Muirhead and Saturnelli, LLC

(57) ABSTRACT

It is an object of the present invention to provide a transmission imager which can produce a transmission image from two or more different view points with the use of a simpler arrangement.

The transmission imager according to the present invention is provided having a radiation source 2 for radiating radioactive rays from its target 2a, a radiation detector, and a specimen table provided between the target 2 and the radiation detector for having a specimen to be examined placed thereon, wherein the radiation detector is arranged with its detecting surface at the center P extending substantially at a right angle to a reference axis L1 or L2 which extends from the center P to the target 2a. In particular, the transmission imager is characterized in that the radiation detector is a combination of two, first and second, radiation detectors 3 and 4. The first radiation detector 3 is arranged to be moved to and from the target 2a by the action of a driving mechanism and thus positioned further from the target 2a than the second radiation detector 4. The radiation source 2 is specifically arranged in relation to the two, first and second, radiation detectors 3 and 4 so that its target 2a comes at an angle to face a cathode 2b which is disposed closer to the second radiation detector 4.

9 Claims, 4 Drawing Sheets (a)

(b)

TRANSMISSION IMAGER

FIELD OF THE INVENTION

The present invention relates to a transmission imager for use in, e.g., transmission imaging inspection of an electronic circuit board. More particularly, it relates to a transmission imager which has a radiation source for radiating radioactive rays from its target, a radiation detector, and a specimen table provided between the target and the radiation detector for having a specimen to be examined placed thereon, wherein the radiation detector is arranged with its detecting surface at the center extending substantially at a right angle to a reference axis which extends from the center to the target.

BACKGROUND OF THE INVENTION

Such a conventional transmission imager is known as disclosed in Japanese Patent Laid-open Publication No. 2001-153819 which includes a first imaging means for producing an X-ray tomographic image and a second imaging means for producing a variable angle transmission image. The conventional transmission imager of the citation has an image intensifier provided fixedly off to a location lower than an X ray radiation source with its detecting surface extending horizontally for producing a tomographic image by X-ray laminography technique. Since the technique is intended to turn the X ray image in synchronization with the rotating movement of a specimen for producing tomographic images at the plane of turning, the detecting surface at the center of the detector is at a right angle to a reference line which extends from the center to the target.

It is however necessary for determining the location of producing a laminography image to prepare a series of transmission images at different angles. This action of preparing the transmission images is commonly carried out by the second imaging means or radiation detector being shifted in its angular position. Accordingly, the radiation detector has to be shifted in a succession to predetermined angles for producing a series of the transmission images at different angles, hence declining the efficiency of the image producing action. Also, its shifting action requires an intricate shifting mechanism thus increasing the overall cost.

It is moreover essential for implementing the conventional apparatus to permit X rays to be radiated throughout a wider angle from the X ray radiation source and received by the laminograph. This requires a transmission type of the X ray radiation source. As the result, the energy of radiation will be declined after passing the target hence producing an image, which is clear at the center and both sides, only with difficulty.

It is an object of the present invention, in view of the above aspect, to provide a transmission imager which can produce a transmission image from two or more different view points with the use of a simpler arrangement.

SUMMARY OF THE INVENTION

A transmission imager according to the present invention is provided having a radiation source for radiating radioactive rays from its target, a radiation detector, and a specimen table provided between the target and the radiation detector for having a specimen to be examined placed thereon, wherein the radiation detector is arranged with its detecting surface at the center extending substantially at a right angle to a reference axis which extends from the center to the target. In particular, the transmission imager is characterized in that the radiation detector is a combination of two, first and second, radiation detectors, the first radiation detector is arranged to be moved to and from the target by the action of a driving mechanism and thus positioned further from the target than the second radiation detector, and the radiation source is specifically arranged in relation to the two, first and second, radiation detectors so that its target comes at an angle to face a cathode which is disposed closer to the second radiation detector.

As the radiation detector is implemented by the first and second radiation detectors of which the detecting surfaces intersect at the center substantially at a right angle to their respective reference axes. This allows the radiation detector to produce a transmission image at minimum distortion from two different angles of view without shifting its angle. Also, the overall arrangement can remain simple.

As the target in the radiation source faces the cathode at an angle, its radiation can stay in a designed range. Also, with the radiation source positioned in relation to the first and second radiation detectors so that its cathode comes closer to the second radiation detector, both the first and second radiation detectors can receive and detect radiations with a minimum decay in their energy.

The transmission imager may be modified in which the radiation source is specifically arranged in relation to the two, first and second, radiation detectors so that its maximum output axis runs along the first one of two reference axes extending from the first radiation detector or between the first reference axis and the other or second reference axis extending from the second radiation detector. This allows both the first and second radiation detectors to receive and detect radiations with a minimum decay in the energy, hence avoiding their transmission image from being declined in the quality.

The transmission imager may be modified in which the second radiation detector is implemented by a flat panel detector. As the flat panel detector is favorably planar at the detecting surface, its perspective transmission image can be minimized in distortion.

The transmission imager may be modified in which the first radiation detector is implemented by an image intensifier. This allows the first radiation detector to be less affected by an output of the radiation source and, even when its location is far from the target, produce a transmission image at desired quality.

The transmission imager according to the present invention has the radiation source arranged with the maximum output axis extending between the first reference axis and the second reference axis, thus permitting no declination in the quality of each transmission image. Also, the transmission imager allows the perspective transmission image to be produced without shifting the angle of the detectors and can thus be simplified in the overall arrangement and improved in the efficiency of its image producing action. Moreover, as the first radiation detector is an image intensifier and the second radiation detector is a flat panel detector, their transmission image can be improved in the quality.

Other objects, arrangements, and features of the present invention will be apparent from the following detailed description of the preferred embodiments.

BRIEF DESCRIPTION OF THE DRAWINGS

FIG. 5a is a profile of the relative output along the X axis and FIG. 5b is a profile of the relative output along the Y axis.

BEST MODES FOR EMBODYING THE INVENTION

Some embodiments of the present invention will be described referring to the accompanying drawings.

Figure 1:
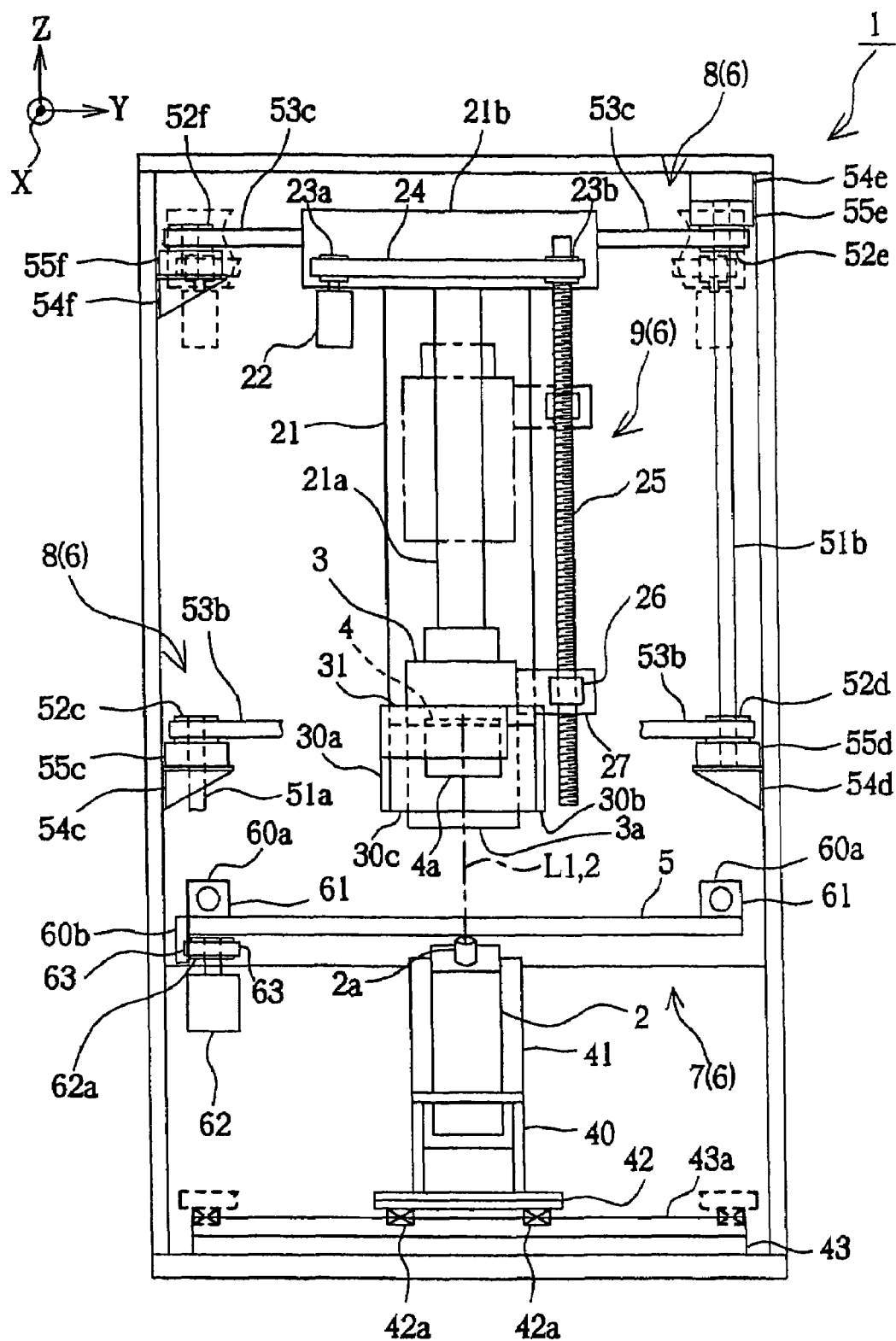
FIG. 1 is a partially broken front view of a transmission imager.
Figure 2:
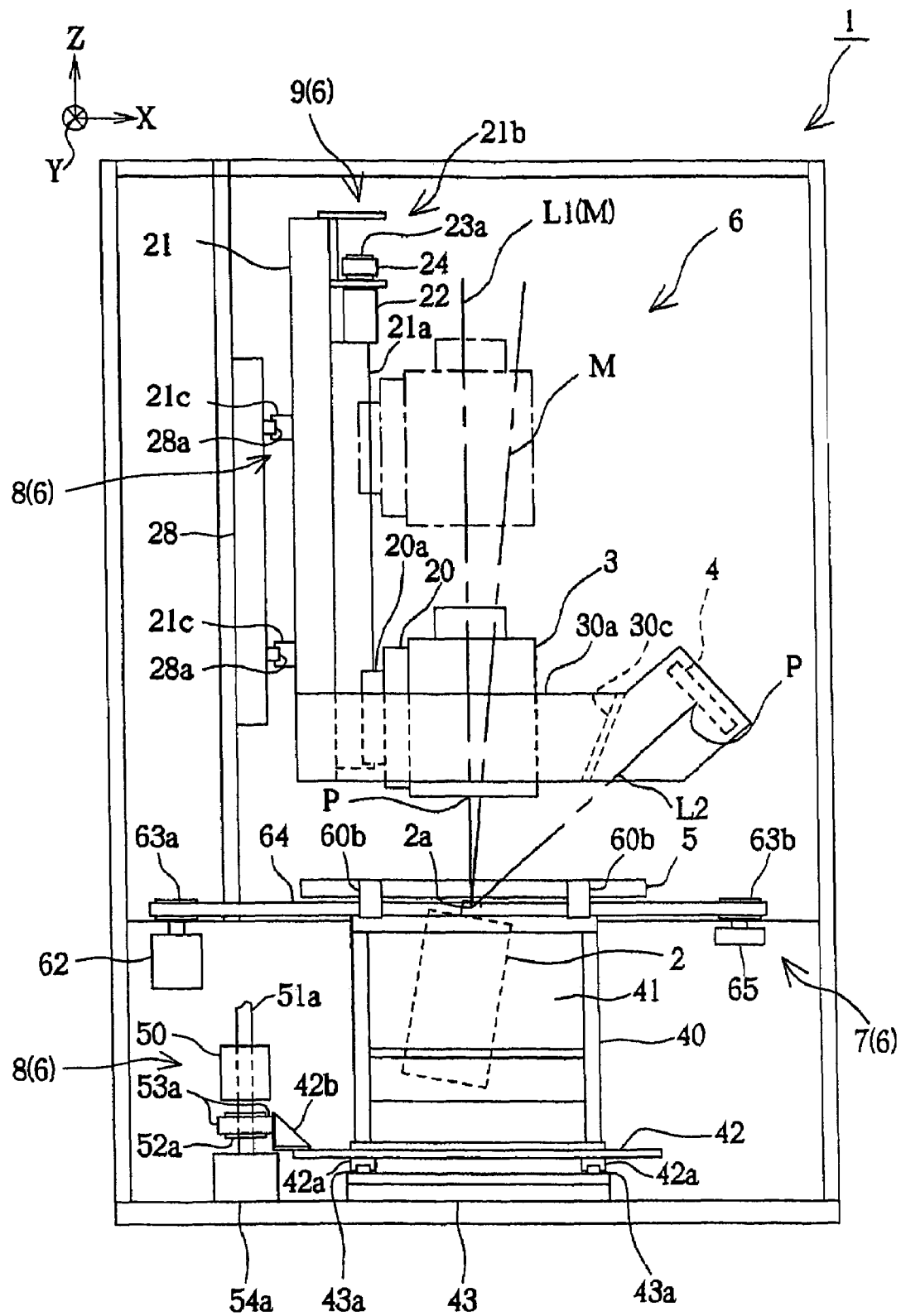
FIG. 2 is a partially broken side view of the transmission imager.
Figure 3:
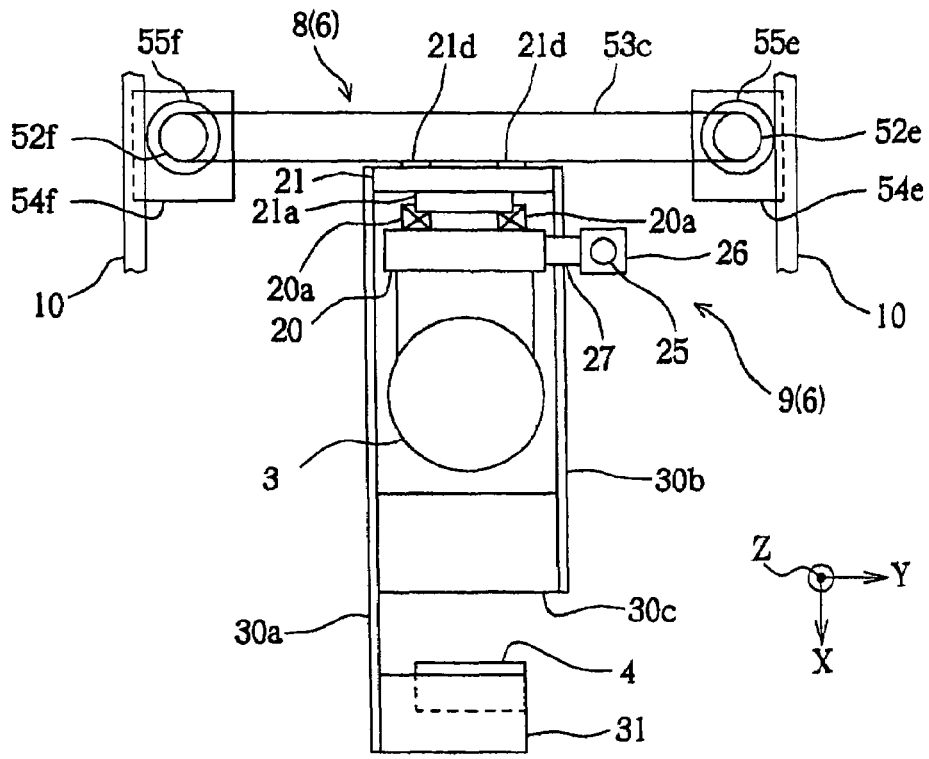
FIG. 3 is a plan view of the transmission imager.

As shown in FIGS. 1 to 3, a transmission imager 1 according to the present invention comprises substantially a radiation source unit 2 equipped with a target 2a for emitting X rays, two, first and second, radiation detectors 3 and 4 for detecting transmitted X rays, a specimen table 5 on which a specimen S is placed, a movement mechanism assembly 6 for moving the two, first and second, radiation detectors 3 and 4 in relation to the specimen table 5, and a housing 10. The movement mechanism assembly 6 includes a table movement mechanism 7 for moving the specimen table 5 horizontally in forward and backward directions along the X axis, a transverse movement mechanism 8 for moving the radiation source 2 and the two, first and second, radiation detectors 3 and 4 horizontally in direction along the Y axis, and a vertical movement mechanism 9 for moving the first radiation detector 3 upward and downward along the Z axis.

The first radiation detector 3 is implemented by an image intensifier (II) which is high in the detective capability. The II 3 may create a bobbin distortion in its image which is corrected with a distortion compensating lens.

The second radiation detector 4 is implemented by a flat panel detector. The flat panel detector 4 has scintillator bonded to a imaging device of pixel matrix type for converting the energy of X rays into light. Since the detecting surface 4a of the flat panel detector 4 where the scintillator is bonded is planer, the produced image represents an perspective transmission image of the specimen S without distortion.

The II 3 is supported by the vertical movement mechanism 9 composed mainly of a movable frame 21, a motor 22, a screwed shaft 25, and a ball screw 26 and fixedly mounted to a mounting plate 20 so that its detecting surface 3a extends at least at the center P at a right angle to the first reference axis L1. The mounting plate 20 has a pair of sliders 20a, 20a mounted to both sides of a slide shaft 21a, which is secured to the movable frame 21, for sliding movement along the Z axis. The movable frame 21 includes an upper frame 21b, a pair of sliders 21c, 21c, and a pair of belt joints 21d, 21d. A driver pulley 23a and a follower pulley 23b are mounted on the upper frame 21b between which a belt 24 is mounted. The driver pulley 23a is joined by the upper frame 21b to the motor 22 while the follower pulley 23b is joined to the screwed shaft 25. This allows the driving force of the motor 22 to transmit via the driver pulley 23a to the belt 24 which in turn rotates the follower pulley 23b and the screwed shaft 25. The screwed shaft 25 is connected to the ball screw 26 which is mounted by a support plate 27 to one side of the mounting plate 20. Accordingly in this arrangement, the screwed shaft 25 is driven by the motor 22 for moving the II 3 along the Z axis.

Referring to FIG. 3, the flat panel detector 4 is mounted to a detector mounting plate 31 which is fixedly joined by a support arm 30a to the movable frame 21, so that its detecting surface 4a at the center extends substantially at a right angle to a second reference axis L2. The support arm 30a is joined by a reinforcement plate 30c to another support arm 30b which has a different length. The two support arms 30a and 30b are also joined to both sides of the movable frame 21 so that the II 3 is accommodated, when viewed from the direction of the Z axis, in a space defined by the support arms 30a and 30b and the reinforcement plate 30c.

As shown in FIGS. 1 and 2, the specimen table 5 is mounted to the table movement mechanism 7 which comprises substantially a motor 62, a driver pulley 63a, a follower pulley 63b, and a belt 64. The table movement mechanism 7 is driven for controlling the image detecting areas of the II 3 and the flat panel detector 4.

The specimen table 5 includes a pair of sliders 60a, 60a provided at both sides thereof and a pair of belt joints 60b, 60b joined to the belt 64. The sliders 60a, 60a are slidably connected to two slide shafts 61, 61 respectively. The belt 64 is mounted between the driver pulley 63a and the follower pulley 63b, which are located at diagonal positions, for traveling in a circle. The driver pulley 63a is driven by the motor 62 mounted to a base 66. This allows the specimen table 5 to move horizontally along the X axis.

The traverse movement mechanism 8 for moving the radiation source 2, the II 3, and the flat panel detector 4 together along the Y axis will now be explained. The traverse movement mechanism 8 comprises substantially a motor 50 for driving the movement, three pairs of pulleys 52a to 52f arranged co-operable with two link shafts Sla and 51b, and three belts 53a to 53c.

The radiation source 2 is mounted to a mounting base 40 which is anchored by a retaining plate 41 to a radiation source frame 42. A pair of sliders 42a, 42a and a pair of belt joints 42b, 42b joined to the belt 53a are mounted on the radiation source frame 42. The two sliders 42a, 42a are slidably connected to two slider shafts 43a, 43a respectively. The belt 53a joined with the two belt joints 42b 42b is mounted between the two pulleys 52a and 52b.

The motor 50 is mounted on a base 54a and joined to the link shaft 51a. As the motor 50 is turned on, the link shaft 51a rotates the pulleys 52a and 52c mounted to both ends thereof respectively. The pulley 52a mounted to the lower end of the link shaft 51a is connected to its counter pulley 52b by the belt 53a joined with the two belt joints 42b, 42b of the radiation source frame 42. The pulley 52c mounted to the upper end of the link shaft 51a is connected by the belt 53b to its counter pulley 52d which is mounted at a diagonal location on the housing 10. The pulley 52d mounted on the housing 10 is joined to the lower end of the link shaft 51b which extends vertically and is joined at the upper end to the pulley 52e. The pulley 52e is connected to its counter pulley 52f by the belt 53c joined with the two belt joints 21d, 21d of the movable frame 21.

The foregoing arrangement allows the single motor 50 to drive the two belts 53a and 53c via the transmitting action of the link shafts 51a and 51b and the pulleys 52a to 52f, thus moving the radiation source 2, the II 3, and the flat panel detector 4 integrally along they axis. This integral movement protects the image detecting area from being displaced. Also, since the integral movement is carried out with the angle of perspective remaining unchanged, the perspective transmission image of any specimen can efficiently be captured at any desired location.

Figure 4:
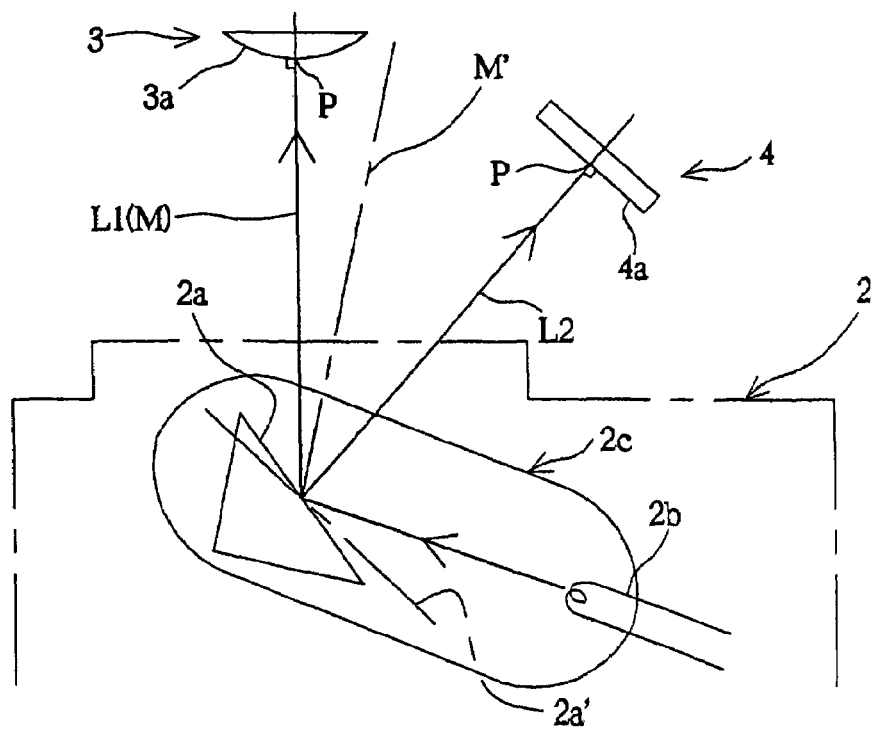
FIG. 4 is a schematic view showing the positional relationship between a first radiation detector, a second radiation detector, a target, a cathode, and a maximum output axis.
Figure 5:
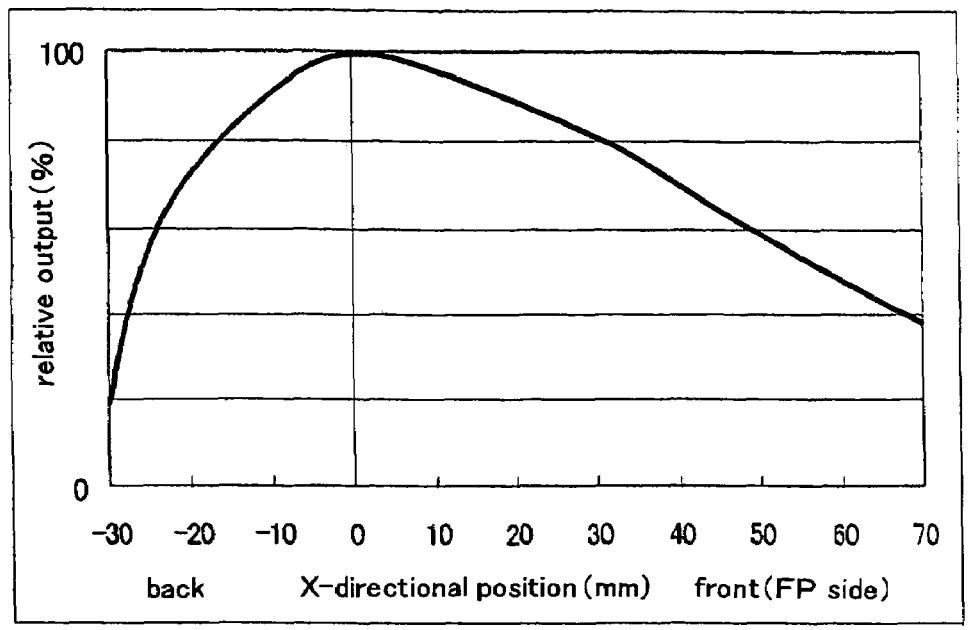
FIG. 5 illustrates graphs of the relative output about the maximum output axis, where
Figure 5:
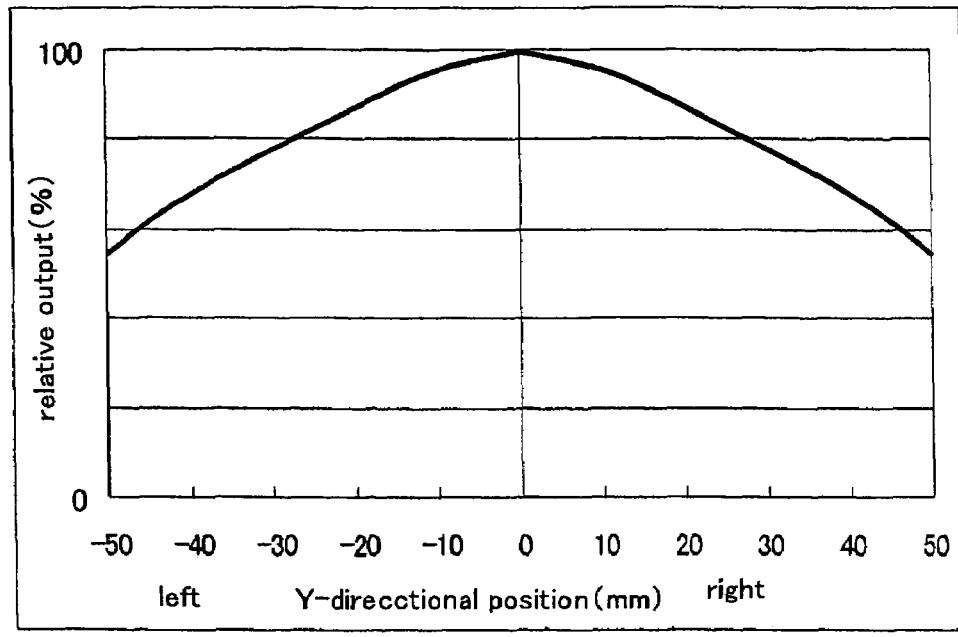

Referring to FIG. 4, the radiation source 2 is arranged with its target 2a generating a range of X rays greater than the effective radiation width V. More specifically, the target 2a generates X rays upon receiving cathode rays emitted from a cathode 2b in a radiation generator 2c. In this embodiment, the radiation source 2 allows the target 2a in the radiation generator 2c to have its surface oriented at an angle to the original target surface 2a' for more opening in relation to its maximum output axis M. As shown in FIG. 5b the output signal characteristic profile along the Y axis is symmetrical about the maximum output. On the other hand, the profile along the X axis is moderate in the attenuation curve at the front side close to the flat panel detector 4.

As the result, the image received by the II 3 remains clear even when locating further from the target 2a while the image received by the flat panel detector 4 which is closer to the target 2a is much clear. It is also desired that the maximum output axis M of the radiation source 2 is sandwiched between the first reference axis L1 extending from the first radiation detector 3 to the target (2a) and the second reference axis L2 extending from the second radiation detector 4 to the target (2a) and simultaneously remains closer to the first reference axis L1 as denoted by M'.

As set forth above, the specimen table 5 is first moved to a desired location by the action of the table movement mechanism 7 and then the radiation source 2, the II 3, and the flat panel detector 4 are integrally moved by the action of the traverse movement mechanism 8 thus to precisely locate the image detecting area and produce the perspective transmission image at higher efficiency. Moreover, when an enlargement of the perspective transmission image is desired, it can be produced with the II 3 being controllably driven by the vertical movement mechanism 9.

Finally, other feasible embodiments of the present invention will briefly be explained.

The previous embodiment allows the radiation source 2, the II 3, and the flat panel detector 4 to be moved integrally along the Y axis while the specimen table 5 is movable along the X axis. Alternatively, while the radiation source 2, the II 3, and the flat panel detector 4 remain all fixed, the specimen table 5 may be arranged movable along both the X and Y axes.

Although the second radiation detector 4 is implemented by a flat panel detector of digital type in the previous embodiment, it may be any device which has a detection surface thereof substantially arranged planer and requires no use of lenses. For example, the second radiation detector 4 is selected from other types of flat panel detector and scan-operable line sensors.

The specimen table 5 of flat-top type is used in the previous embodiment but not intended to be so limited. For example, the specimen table 5 may have a curved surface thereof arranged to match a spherical shape of specimen.

While the radiation source 2 is also not limited to an X-ray generator, its target may be provided for emitting any type of radioactive rays.

It would be understood that the numerals depicted in the appended claims are illustrative only for denoting the components in the relevant drawings and the present invention is not limited to the embodiment shown in the accompanying drawings.

INDUSTRIAL APPLICATIONS

The present invention is directed towards any type of transmission imaging apparatus for carrying out the action of transmission imaging inspection over a specimen with the use of radioactive rays. For example, the transmission imager according to the present invention may be provided for examining the soldering of an electronic circuit board as well as the wetting condition of wires or chips and/or the resin molding of a semiconductor device or electronic component.

The invention claimed is:

1. A transmission imager, comprising:
    a radiation source for radiating radioactive rays from a target;
    a radiation detector; and
    a specimen table provided between the target and the radiation detector for having a specimen to be examined placed thereon,
    wherein the radiation source generates X-rays, the X-rays being generated by the target upon receiving cathode rays emitted from a cathode, wherein a range of the X-rays generated is greater than an effective radiation width;
    wherein the radiation detector is a combination of two, first and second, radiation detectors for detecting transmitted X-rays, the first radiation detector arranged with a detecting surface at a center of the first radiation detector extending substantially at a right angle to a first reference axis which extends from said center to the target, and the second radiation detector arranged with a detecting surface at a center of the second radiation detector extending substantially at a right angle to a second reference axis which extends from said center to the target, the first radiation detector arranged to be moved to and from the target by the action of a driving mechanism and thus positioned further from the target than the second radiation detector, and
    wherein the radiation source is specifically arranged in relation to the two, first and second, radiation detectors so that its target comes at an angle to face a cathode which is disposed closer to the second radiation detector.

2. A transmission imager according to claim 1, wherein the radiation source is specifically arranged in relation to the two, first and second, radiation detectors so that a maximum output axis runs along the first one of two reference axes extending from the first radiation detector or between the first reference axis and the other or second reference axis extending from the second radiation detector.

3. A transmission imager according to claim 1, wherein the second radiation detector is a flat panel detector.

4. A transmission imager according to claim 1, wherein the first radiation detector is an image intensifier.

5. A transmission imager according to claim 2, wherein the second radiation detector is a flat panel detector.

6. A transmission imager according to claim 2, wherein the first radiation detector is an image intensifier.

7. A transmission imager according to claim 3, wherein the first radiation detector is an image intensifier.

8. A transmission imager according to claim 4, wherein the first radiation detector is an image intensifier.

9. A transmission imager according to claim 5, wherein the first radiation detector is an image intensifier.

* * * * *